United States Patent [19]

Rodewald et al.

[11] Patent Number: 4,709,114

[45] Date of Patent: Nov. 24, 1987

[54] CATALYTIC OXYGENATE CONVERSION

[75] Inventors: Paul G. Rodewald, Rocky Hill, N.J.; Ernest W. Valyocsik, Yardley, Pa.

[73] Assignee: Mobil Oil Corporation, New York, N.Y.

[21] Appl. No.: 905,996

[22] Filed: Sep. 11, 1986

Related U.S. Application Data

[63] Continuation-in-part of Ser. No. 749,242, Jun. 27, 1985, abandoned, which is a continuation-in-part of Ser. No. 705,821, Feb. 26, 1985, abandoned.

[51] Int. Cl.$^4$ .......................... C07C 1/00; C07C 11/20
[52] U.S. Cl. .................................... 585/640; 585/408; 585/733
[58] Field of Search ........................ 585/640, 733, 408

[56] References Cited

U.S. PATENT DOCUMENTS

| | | | |
|---|---|---|---|
| 3,702,886 | 11/1972 | Argauer et al. | 423/328 |
| 4,287,166 | 9/1981 | Dwyer et al. | 423/328 |
| 4,427,787 | 1/1984 | Miale et al. | 502/71 |
| 4,483,835 | 11/1984 | Zones | 423/328 |
| 4,621,161 | 11/1986 | Shihabi | 585/640 |

OTHER PUBLICATIONS

Lok et al, *Zeolites,* 1983, vol. 3, pp. 282–291.

*Primary Examiner*—Curtis R. Davis
*Attorney, Agent, or Firm*—Alexander J. McKillop; Michael G. Gilman; Dennis P. Santini

[57] ABSTRACT

A process is provided for converting feedstock comprising oxygenates to product comprising hydrocarbons over a catalyst comprising zeolite ZSM-58.

19 Claims, No Drawings

CATALYTIC OXYGENATE CONVERSION

CROSS-REFERENCE TO RELATED APPLICATION

This application is a continuation-in-part of application Ser. No. 749,242, filed June 27, 1985, and now abandoned, which is a continuation-in-part of application Ser. No. 705,821, filed Feb. 26, 1985 and now abandoned.

BACKGROUND OF THE INVENTION

1. Field of the Invention

This invention relates to a process for conversion of feedstock comprising lower aliphatic alcohols, carbonyls, ethers or analogues thereof to product comprising hydrocarbons. The process comprises contacting, under conversion conditions, said feedstock with a catalyst comprising a synthetic, thermally stable, molecular shape selective, active form of crystalline material designated ZSM-58.

2. Description of Prior Art

Zeolitic materials, both natural and synthetic, have been demonstrated in the past to have catalytic properties for various types of hydrocarbon conversions. Certain zeolitic materials are ordered, porous crystalline aluminosilicates having a definite crystalline structure within which there are a large number of smaller cavities which may be interconnected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra containing aluminum is balanced by the inclusion in the crystal of a cation, for example, an alkali metal or an alkaline earth metal cation. This can be expressed wherein the ratio of aluminum to the number of various cations, such as Ca/2, Sr/2, Na, K or Li is equal to unity. One type of cation may be exchanged either entirely or partially by another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic aluminosilicates. These aluminosilicates have come to be designated by convenient symbols, as illustrated by zeolite ZSM-5 (U.S. Pat. No. 3,702,886).

The use of certain zeolites as catalyst components is taught in U.S. Pat. No. 4,305,808, for example.

The silica-to-alumina ratio of a given zeolite is often variable; for example, zeolite X (U.S. Pat. No. 2,882,244) can be synthesized with a silica-to-alumina ratio of from 2 to 3; zeolite Y (U.S. Pat. No. 3,130,007) from 3 to about 6. In some zeolites, the upper limit of silica-to-alumina ratio is virtually unbounded. Zeolite ZSM-5 is one such material wherein the silica-to-alumina ratio is at least 5. U.S. Pat. No. 3,941,871 discloses a crystalline metal organo silicate essentially free of aluminum and exhibiting an x-ray diffraction pattern characteristic of ZSM-5 type aluminosilicate. U.S. Pat. Nos. 4,061,724; 4,073,865 and 4,104,294 describe microporous crystalline silicas or organo silicates wherein the aluminum content present is at lower levels.

A number of U.S. patents teach heteroatom feed conversion. Examples of these are U.S. Pat. Nos. 3,894,104, 3,894,106, 3,894,107, 3,899,544, 3,965,205, 4,046,825, 4,156,698 and 4,311,865. Methanol is converted to gasoline in U.S. Pat. Nos. 4,302,619, 3,928,483 and 4,058,576 as examples. Methanol is converted to olefins and/or aromatics in, for example, U.S. Pat. Nos. 3,911,041, 4,025,571, 4,025,572, 4,025,575 and 4,049,735.

SUMMARY OF THE INVENTION

The present invention relates to a novel process for converting organic compounds such as lower aliphatic alcohols, carbonyls, ethers or analogues thereof to hydrocarbons over a catalyst comprising zeolite ZSM-58.

DESCRIPTION OF SPECIFIC EMBODIMENTS

The contents of applications Ser. No. 705,821, filed Feb. 26, 1985, and 749,242, filed June 27, 1985, are entirely incorporated herein by reference.

The feedstock to the present process comprises lower aliphatic alcohols, carbonyls, ethers or mixtures thereof. Feedstock alcohols will be aliphatic alcohols of from 1 to about 6 carbon atoms, preferably from 1 to 3 carbon atoms, e.g., methanol and ethanol. Feedstock carbonyls will be lower aliphatic carbonyls, such as, for example, acetone. Feedstock ethers will be lower aliphatic ethers of up to about 6 carbon atoms, e.g., from 2 to about 6 carbon atoms, such as dimethylether, n-propyl ether, p-dioxane, trioxane and hexose.

The product of this process will be predominantly hydrocarbons including olefins of from 2 to 5 or more carbon atoms with $C_2$ olefins usually less than about 10% of the total and $C_5+$ olefins usually less than about 15% of the total. Aromatic hydrocarbons, such as durene, are also produced. $C_2$, $C_3$ and $C_4$ olefins are desired chemical products, and $C_5+$ products are valuable as gasoline components.

In general, the feedstock is converted by the present process to hydrocarbons, e.g., olefins, and hydrocarbons including aromatics, e.g., gasoline components, with reaction conditions including a temperature of from about 150° C. to about 600° C., a pressure of from about 0.5 atmosphere to about 50 atmospheres and a weight hourly space velocity of from about 0.5 $hr^{-1}$ to 100 $hr.^{-1}$.

The present process requires a catalyst comprising the synthetic, thermally stable, molecular shape selective crystalline ZSM-58.

The structure of ZSM-58 is distinguished from other crystalline silicates by a unique X-ray diffraction pattern. The typical X-ray diffraction pattern intensities for ZSM-58 are shown in Table 1, hereinafter.

The crystalline silicate ZSM-58 for use herein has a composition involving silica and alumina in the relationship:

$$(0.1-2)Al_2O_3:(100)SiO_2.$$

In the as-synthesized form, ZSM-58 has a formula, on an anhydrous basis and in terms of moles of oxides per 100 moles of silica, as follows:

$(0.1-2.0)R_2O:(0.2-1.0)M_{2/n}O:(0.1-2)Al_2O_3:(100-)SiO_2$ wherein M is an alkali or alkaline earth metal cation, n is the valence of M, and R is an organic cation. M and $R_2O$ may be removed from the composition by appropriate treatment.

TABLE 1

| Interplanar d-Spacing (A) | | Relative Intensity, I/Io |
|---|---|---|
| 13.70 | ±0.20 | W |
| 11.53 | ±0.20 | W-VS |
| 10.38 | ±0.20 | W |
| 7.82 | ±0.14 | W-VS |
| 6.93-6.79 | ±0.14 | W-VS |
| 6.19 | ±0.14 | W-VS |
| 5.94 | ±0.12 | W-M |
| 5.77 | ±0.12 | VS |
| 5.22 | ±0.12 | W |
| 5.18 | ±0.10 | VS |
| 4.86 | ±0.09 | M-S |
| 4.72 | ±0.08 | S |
| 4.57 | ±0.08 | W |
| 4.51 | ±0.08 | S |
| 4.43 | ±0.08 | W |
| 4.19 | ±0.08 | W |
| 4.15 | ±0.08 | M |
| 4.00 | ±0.07 | W |
| 3.97 | ±0.07 | W |
| 3.89 | ±0.07 | W |
| 3.84 | ±0.07 | M |
| 3.81 | ±0.07 | W-M |
| 3.59 | ±0.06 | W |
| 3.46 | ±0.06 | W-M |
| 3.41 | ±0.06 | S-VS |
| 3.36 | ±0.06 | S-VS |
| 3.32 | ±0.06 | M-S |
| 3.29 | ±0.05 | W |
| 3.17 | ±0.05 | W-M |
| 3.07 | ±0.05 | W-M |
| 3.05 | ±0.05 | W-M |
| 3.01 | ±0.05 | W-M |
| 2.88 | ±0.05 | W |
| 2.85 | ±0.05 | W |
| 2.75 | ±0.05 | W |
| 2.67 | ±0.04 | W |
| 2.60 | ±0.04 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, $100\ I/I_o$, where $I_o$ is the intensity of the strongest line or peak, and d (obs.) the interplanar spacing in Angstrom Units (A), corresponding to the recorded lines, were determined. In Table 1, the relative intensities are given in terms of the symbols W=weak, M=medium, S=strong and VS=very strong. In terms of intensities, these may be generally designated as follows:

W=0-20
M=20-40
S=40-60
VS=60-100

It should be understood that this X-ray diffraction pattern is characteristic of all the species of ZSM-58 compositions. The sodium form as well as other cationic forms reveal substantially the same pattern with some minor shifts in interplanar spacing and variation in relative intensity. Other minor variations can occur, depending on the silicon to aluminum ratio of the particular sample, as well as its degree of thermal treatment. Multiplets may be observed in the typical X-ray pattern for ZSM-58 at d-spacing values of 6.93-6.79±0.14, 4.86±0.09, 3.41±0.06, 3.07±0.05 and 3.01±0.05 Angstroms.

The original alkali or alkaline earth metal cations of the as synthesized ZSM-58 can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which render the ZSM-58 more catalytically active for the present reaction. These include hydrogen, rare earth metals and metals of Groups IIA, IIIA, IVA, IB, IIB, IIIB, IVB, VIB and VIII of the Periodic Table of the Elements.

Typical ion exchange technique would be to contact the synthetic ZSM-58 with a salt of the desired replacing cation or cations. Examples of such salts include the halides, e.g. chlorides, nitrates and sulfates.

The crystalline silicate ZSM-58 can also be used in the present process in intimate combination with a hydrogenating component such as tungsten, vanadium, molybdenum, rhenium, nickel, cobalt, chromium, manganese, or a noble metal such as platinum. Such component can be exchanged into the composition to the extent aluminum is in the structure, impregnated therein or intimately physically admixed therewith. Such component can be impregnated in or on to it such as for example, by, in the case of platinum, treating the ZSM-58 with a solution containing a platinum metal-containing ion. Thus, suitable platinum compounds include chloroplatinic acid, platinous chloride and various compounds containing the platinum amine complex.

The crystalline silicate ZSM-58, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product is particularly useful in the present process.

The ZSM-58 should be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing ZSM-58 in a vacuum, but a longer time is required to obtain a sufficient amount of dehydration.

The ZSM-58 can be prepared from a reaction mixture containing sources of an alkali or alkaline earth metal oxide, an oxide of aluminum, an oxide of silicon, an organic cation of a methyltropinium salt, e.g. halide, hydroxide, sulfate, etc., and water, said reaction mixture having a composition, in terms of mole ratios of oxides, within the following ranges:

| Reactants | Useful | Preferred |
| --- | --- | --- |
| SiO$_2$/Al$_2$O$_3$ | 50–1000 | 70–500 |
| H$_2$O/SiO$_2$ | 5–200 | 10–100 |
| OH$^-$/SiO$_2$ | 0–2.0 | 0.10–1.0 |
| M/SiO$_2$ | 0.01–3.0 | 0.10–1.0 |
| R/SiO$_2$ | 0.01–2.0 | 0.10–0.50 | wherein R and M are as above defined.

Crystallization of the ZSM-58 can be carried out at either static or stirred condition in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered. The reaction mixture can be prepared utilizing materials which supply the appropriate oxides. Such materials may include sodium silicate, silica hydrosol, silica gel, silicic acid, sodium hydroxide, a source of aluminum, and the methyltropinium salt directing agent. The methyltropinium salt may be synthesized by selective methylation of 3-tropanol at the bridgehead nitrogen. This salt has the following formula:

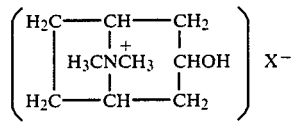

wherein X is an anion, such as, for example, a halide (e.g. iodide, chloride or bromide), nitrate, hydroxide, sulfate, bisulfate, perchlorate, etc. U.S. application Ser. No. 705,820, filed Feb. 26, 1985 teaches these salts and their synthesis and is incorporated herein by reference.

It should be realized that the reaction mixture oxides can be supplied by more than one source. The reaction mixture can be prepared either batchwise or continuously. Crystal size and crystallization time of the new crystalline material will vary with the nature of the reaction mixture employed and the crystallization conditions.

In all cases, synthesis of the ZSM-58 crystals is facilitated by the presence of at least 0.01 percent, preferably 0.10 percent and still more preferably 1 percent, seed crystals (based on total weight) of crystalline product.

The crystals prepared as above can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In practicing the desired chemical conversion process, it may be useful to composite the crystalline zeolite ZSM-58 with matrix-comprising material resistant to the temperature and other conditions employed in the process. Such matrix material is useful as a binder and imparts additional resistance to the catalyst for the temperature, pressure and reactant feed stream velocity conditions allowed in the present process. The composite may be in the form of an extrudate.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families which include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing matrix materials, the catalyst employed herein may be composited with a porous matrix material such as alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of activity enhanced zeolite component and matrix, on an anhydrous basis, may vary widely with the zeolite content of the dry composite ranging from about 1 to about 99 percent by weight and more usually in the range of about 5 to about 80 percent by weight.

In order to more fully illustrate the nature of the invention and the manner of practicing same, the following examples are presented. In the examples, whenever sorption data are set forth for comparison of sorptive capacities for cyclohexane and/or n-hexane, they were measured on an electrobalance as follows:

The adsorbate was activated at 500° C. in flowing helium until at constant weight. Adsorptions were conducted at 90° C., with the hydrocarbon containing helium gas stream flowing around the sample. Partial pressures of hexane and cyclohexane were 28 and 35 torr, respectively. The measurements were continued until the sample reached constant weight. The increase in weight was converted to adsorption capacity of the sample in g/100 g of activated zeolite.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078 and in *The Journal of Catalysis*, Vol. IV, pp. 527–529 (August 1965), each incorporated herein as to that description. The relationship of Alpha Value to the intrinsic rate constants for many acid-catalyzed reactions, such as that of the present invention, is detailed in "The Active Site of Acidic Aluminosilicate Catalysts," *Nature*, Vol. 309, No. 5969, pp. 589–591, 14 June 1984 incorporated herein by reference as to that detail.

EXAMPLES 1–6

Six separate synthesis reaction mixtures were prepared with compositions indicated in Table 2. The mixtures were prepared with silica sol (30 percent SiO$_2$), NaAlO$_2$, NaOH, a methyltropinium salt, i.e. iodide, and water. The mixtures were maintained at 160° C. for 4 days in a stainless steel, stirred (400 rpm) autoclave at autogenous pressure. Solids were separated from any unreacted components by filtration and then water washed, followed by drying at 110° C. The product crystals were analyzed by X-ray diffraction and chemical analysis. The product of Example 1 was found to be crystalline ZSM-58 with a trace of unidentified second component impurity. The products from Examples 2-6 proved to be 100 percent crystalline ZSM-58.

The X-ray diffraction pattern of the Example 4 crystals, after calcination at 538° C. for 17 hours in air, is set forth as illustration in Table 3. Other properties of each crystalline product are presented in Table 4. In the latter table, compositions are calculated on the basis of 100 ($SiO_2+AlO_2^-$) tetrahedra. The as-synthesized ZSM-58 from these examples contains from 3.8 to 5.0 methyltropinium cations per 100 tetrahedra.

TABLE 2

| Example | Mixture Composition (mole ratios) | | | | |
| --- | --- | --- | --- | --- | --- |
| | $SiO_2$/$Al_2O_3$ | $H_2O$/$SiO_2$ | $OH^-$/$SiO_2$ | $Na^+$/$SiO_2$ | $R^*$/$SiO_2$ |
| 1 | 300 | 40 | 0.30 | 0.31 | 0.25 |
| 2 | 200 | 40 | 0.30 | 0.31 | 0.25 |
| 3 | 90 | 40 | 0.40 | 0.42 | 0.25 |
| 4 | 90 | 40 | 0.30 | 0.32 | 0.25 |
| 5 | 90 | 40 | 0.30 | 0.32 | 0.25 |
| 6 | 70 | 40 | 0.30 | 0.33 | 0.25 |

*R = methyltropinium cation.

TABLE 3

| d(A) | Observed 2 Theta | Relative Intensity |
| --- | --- | --- |
| 13.57 | 6.511 | 7.4 |
| 11.44 | 7.721 | 51.2 |
| 10.29 | 8.588 | 4.1 |
| 7.76 | 11.389 | 53.6 |
| 6.89 | 12.834 | 60.1 |
| 6.84 | 12.932 | 33.0 |
| 6.15 | 14.378 | 57.8 |
| 5.91 | 14.987 | 19.5 |
| 5.74 | 15.435 | 85.8 |
| 5.16 | 17.173 | 100.0 |
| 4.84 | 18.317 | 51.9 |
| 4.70 | 18.865 | 56.0 |
| 4.52 | 19.612 | 20.3 |
| 4.49 | 19.755 | 51.7 |
| 4.41 | 20.093 | 4.7 |
| 4.13 | 21.186 | 26.0 |
| 3.98 | 22.307 | 11.8 |
| 3.96 | 22.404 | 8.9 |
| 3.87 | 22.969 | 17.1 |
| 3.82 | 23.268 | 30.6 |
| 3.80 | 23.365 | 25.6 |
| 3.57 | 24.882 | 16.2 |
| 3.44 | 25.849 | 35.2 |
| 3.38 | 26.303 | 96.5 |
| 3.35 | 26.546 | 86.7 |
| 3.34 | 26.619 | 80.8 |
| 3.30 | 26.947 | 66.2 |
| 3.28 | 27.158 | 9.1 |
| 3.16 | 28.237 | 23.3 |
| 3.06 | 29.159 | 26.8 |
| 3.06 | 29.176 | 31.2 |
| 3.03 | 29.406 | 22.7 |
| 2.996 | 29.816 | 25.2 |
| 2.988 | 29.901 | 21.2 |
| 2.870 | 31.158 | 4.1 |
| 2.842 | 31.473 | 5.1 |
| 2.664 | 33.638 | 5.5 |
| 2.589 | 34.643 | 4.8 |
| 2.503 | 35.869 | 4.3 |
| 2.488 | 36.099 | 6.3 |
| 2.438 | 36.863 | 9.0 |
| 2.421 | 37.134 | 14.9 |
| 2.390 | 37.626 | 5.8 |
| 2.354 | 38.230 | 2.8 |
| 2.332 | 38.591 | 4.3 |
| 2.300 | 39.161 | 16.7 |
| 2.236 | 40.319 | 2.4 |
| 2.231 | 40.413 | 1.9 |
| 2.211 | 40.807 | 3.2 |
| 2.164 | 41.739 | 1.7 |
| 2.111 | 42.836 | 1.4 |
| 2.073 | 43.660 | 3.0 |
| 2.039 | 44.427 | 0.3 |
| 1.977 | 45.880 | 11.4 |
| 1.950 | 46.568 | 4.4 |
| 1.932 | 47.030 | 3.9 |
| 1.915 | 47.476 | 3.7 |
| 1.838 | 49.594 | 6.4 |
| 1.835 | 49.667 | 5.5 |

TABLE 4

| Example | Moles C/Mole N | Moles per Mole $Al_2O_3$ | | | COMPOSITION | | | |
| --- | --- | --- | --- | --- | --- | --- | --- | --- |
| | | $N_2O$ | $Na_2O$ | $SiO_2$ | Al 100 $T_d$ | $Na^+$ 100 $T_d$ | $N^+$ 100 $T_d$ | R 100 $T_d$ |
| 1 | 9.5 | 4.09 | 0.85 | 223 | 0.89 | 0.76 | 3.6 | 3.8 |
| 2 | 11.2 | 2.43 | 0.74 | 140 | 1.4 | 1.0 | 3.4 | 4.2 |
| 3 | 9.6 | 1.85 | 0.13 | 83 | 2.4 | 0.30 | 4.4 | 4.7 |
| 4 | 10.2 | 1.69 | 0.12 | 78 | 2.5 | 0.30 | 4.2 | 4.8 |
| 5 | 10.8 | 1.77 | 0.25 | 85 | 2.3 | 0.58 | 4.1 | 4.9 |
| 6 | 9.6 | 1.50 | 0.10 | 62 | 3.1 | 0.30 | 4.7 | 5.0 |

EXAMPLE 7

A sample of the Example 4 product crystals, having been calcined in nitrogen for 4 hours at 500° C., ammonium exchanged and then converted to the hydrogen form, was subjected to the sorption test. Significant n-hexane, i.e. 8 weight percent at 90° C., was sorbed while only minimal cyclohexane (about 1 weight percent at 90° C.) was sorbed. This indicates molecular shape selectivity for the ZSM-58.

EXAMPLE 8

The sample of Example 4 product used for sorption evaluation was evaluated in the Alpha Test. Its Alpha Value proved to be 13 at 538° C.

EXAMPLE 9

A feedstock comprising methanol was passed over 1.0 gram of ZSM-58 product of Example 7 at conversion conditions including atmospheric pressure, 371° C. and 4 hr$^{-1}$ WHSV. Conversion of the methanol was 100% with reaction product components listed below:

| Component | Wt. % |
| --- | --- |
| Methane | 2.6 |
| Ethane | 1.5 |
| Ethylene | 5.2 |
| Propane | 14.8 |
| Propylene | 15.8 |
| i-Butane | 1.7 |
| n-Butane | 2.1 |
| Butenes | 24.8 |
| $C_5$ Paraffins & Olefins(P&O) | 1.2 |
| $C_6$ P&O | 14.7 |
| $C_7$ P&O | 7.7 |
| $C_8$ P&O | 5.9 |
| $C_9$ P&O | 0.7 |
| Benzene | 0.1 |
| Toluene | 0.3 |
| Xylenes | 0.6 |

| Component | Wt. % |
| --- | --- |
| C$_9$ Aromatics | 0.3 |

The product from this conversion reaction demonstrates utility for manufacture of a wide range of useful products. For instance, 4.1 wt. % C$_1$–C$_2$ paraffins, useful as fuel gas, were formed. The product included 18.6 wt. % C$_3$–C$_4$ paraffins, useful as LPG, and 45.8 wt. % C$_2$–C$_4$ olefins, useful as petrochemicals. The product also contained 31.5 wt. % C$_5$+ gasoline components.

What is claimed is:

1. A process for converting a feedstock comprising organic compounds selected from the group consisting of alcohol, carbonyl, ether and mixtures thereof to conversion product comprising hydrocarbon compounds, which comprises contacting said feedstock at conversion conditions including a temperature of from about 150° C. to about 600° C., a pressure of from about 0.5 atmosphere to about 50 atmospheres and a weight hourly space velocity of from about 0.5 hr$^{-1}$ to about 100 hr$^{-1}$ with a catalyst composition comprising crystalline zeolite ZSM-58.

2. The process of claim 1 wherein said zeolite has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

3. The process of claim 2 wherein said replacing cations are hydrogen or hydrogen precursor.

4. The process of claim 1 wherein said catalyst composition comprises said zeolite and a matrix.

5. The process of claim 2 wherein said catalyst composition comprises said zeolite and a matrix.

6. The process of claim 4 wherein said matrix is alumina-containing material.

7. The process of claim 5 wherein said matrix is alumina-containing material.

8. The process of claim 4 wherein said catalyst composition is in the form of an extrudate.

9. The process of claim 4 wherein said catalyst composition is in the form of beads.

10. The process of claim 1 wherein said feedstock comprises methanol.

11. The process of claim 10 wherein said zeolite has been treated to replace original cations, at least in part, with cations selected from the group consisting of hydrogen and hydrogen precursors.

12. The process of claim 10 wherein said catalyst composition comprises said zeolite and a matrix.

13. The process of claim 12 wherein said matrix is alumina-containing material.

14. A process for converting a feedstock comprising organic compounds selected from the group consisting of alcohol of from 1 to about 6 carbon atoms, lower aliphatic carbonyl, ether of from 2 to about 6 carbon atoms and mixtures thereof to conversion product comprising hydrocarbon compounds, which comprises contacting said feedstock at conversion conditions including a temperature of from about 150° C. to about 600° C., a pressure of from about 0.5 atmosphere to about 50 atmospheres and a weight hourly space velocity of from about 0.5 hr$^{-1}$ to about 100 hr$^{-1}$ with a catalyst composition comprising crystalline zeolite ZSM-58.

15. The process of claim 14 wherein said zeolite has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

16. The process of claim 15 wherein said replacing cations are hydrogen or hydrogen precursor.

17. The process of claim 14 wherein said catalyst composition comprises said zeolite and a matrix.

18. The process of claim 17 wherein said matrix is alumina-containing material.

19. The process of claim 14 wherein said feedstock comprises alcohol of from 1 to 3 carbon atoms.

* * * * *